United States Patent [19]

Fischer

[11] 4,264,766

[45] Apr. 28, 1981

[54] IMMUNOLOGICAL DIAGNOSTIC REAGENTS

[75] Inventor: Ernst A. Fischer, Münchenstein, Switzerland

[73] Assignee: Hoffmann-La Roche Inc., Nutley, N.J.

[21] Appl. No.: 940,931

[22] Filed: Sep. 11, 1978

[30] Foreign Application Priority Data

Sep. 19, 1877 [GB] United Kingdom ............... 33894/77

[51] Int. Cl.³ .............................................. C07H 5/06
[52] U.S. Cl. .......................................... 536/51; 260/8; 260/112 R; 260/112.5 R; 260/29.6; 424/12; 424/13; 424/78; 424/88; 424/100; 424/105; 424/177; 424/180; 536/1; 536/18; 536/30; 536/45; 536/46; 536/56; 536/102; 536/103; 536/112; 536/47
[58] Field of Search ....................... 536/51, 46, 45, 18, 536/56, 30, 102, 112, 103, 47, 1; 260/29.6 ME, 29.6 PM; 424/12

[56] References Cited

U.S. PATENT DOCUMENTS

| | | | |
|---|---|---|---|
| 2,988,455 | 6/1961 | Rosenberg et al. | 536/112 |
| 3,208,994 | 9/1965 | Flodin | 536/112 |
| 3,236,732 | 2/1966 | Arquilla | 424/12 |
| 3,236,792 | 2/1966 | Curtis | 536/51 |
| 3,277,025 | 10/1966 | Flodin et al. | 536/51 |
| 3,551,555 | 12/1970 | Schuurs | 424/12 |
| 3,790,520 | 2/1974 | Ludwig | 260/29.6 ME |
| 3,833,555 | 9/1974 | Keys et al. | 536/51 |
| 3,857,931 | 12/1974 | Hager | 424/12 |
| 3,860,573 | 1/1975 | Honkanen et al. | 536/51 |
| 3,865,807 | 2/1975 | Narang et al. | 536/51 |
| 3,947,352 | 3/1976 | Cuatrecasas et al. | 536/51 |
| 4,012,570 | 3/1977 | Dean et al. | 536/51 |
| 4,045,384 | 8/1977 | Dorman | 260/8 |
| 4,046,723 | 9/1977 | Dorman | 424/12 |
| 4,053,440 | 10/1977 | Bonnet et al. | 260/29.6 ME |
| 4,094,832 | 6/1978 | Soderberg | 536/51 |
| 4,094,833 | 6/1978 | Johansson et al. | 536/51 |
| 4,111,881 | 9/1978 | Paul | 260/29.6 ME |
| 4,140,662 | 2/1979 | Reckel et al. | 424/12 |
| 4,181,636 | 1/1980 | Fischer | 424/112 |

FOREIGN PATENT DOCUMENTS

| | | | |
|---|---|---|---|
| 2612948 | 10/1976 | Fed. Rep. of Germany | 424/12 |
| 2651680 | 5/1977 | Fed. Rep. of Germany | 424/12 |
| 825421 | 12/1959 | United Kingdom | 424/12 |
| 1031140 | 5/1966 | United Kingdom | 260/8 |
| 1037782 | 8/1966 | United Kingdom | 260/8 |
| 1059847 | 2/1967 | United Kingdom | 424/12 |
| 1117126 | 6/1968 | United Kingdom | 260/8 |
| 1161352 | 8/1969 | United Kingdom | 424/12 |
| 1426284 | 2/1976 | United Kingdom | 424/12 |
| 1495845 | 12/1977 | United Kingdom | 424/12 |

OTHER PUBLICATIONS

Lapedes, "Dictionary of Scientific and Technical Terms", McGraw-Hill Book Co., New York pp. 503–504.
Hawley "The Condensed Chemical Dictionary", Reinhold Co., New York, p. 501.

*Primary Examiner*—Johnnie R. Brown
*Attorney, Agent, or Firm*—Jon S. Saxe; George M. Gould; William H. Epstein

[57] ABSTRACT

A water-insoluble immunological reagent being formed from discrete particles of a latex carrier to which a water-soluble polyhydroxy compound is covalently bound having condensed thereto through a covalent link an immunologically active material; process for the manufacture of said reagent; a kit containing said reagent and the use of said reagent in immunological determinations.

15 Claims, No Drawings

IMMUNOLOGICAL DIAGNOSTIC REAGENTS

BACKGROUND OF INVENTION

The diagnosis of pathological states or other conditions in human beings as well as animals is more and more accomplished by the application of immunological principles, utilized to determine the presence of antibodies or antigens in a body fluid of the subject.

Within the various known testing procedures like the agglutinationtest, the radioimmunoassay, the enzymeimmunoassay, the immunofluorescence or the immunodiffusion, the agglutinationtest is considered as being cheapest, most simple and quick.

In an agglutinationtest, carriers are utilized in order to make it possible to visually or photometrically discern the formed antigen-antibody complexes which have very small sizes. Among the carriers which have been employed are sheep and human erythrocytes, bacterial cells, bentonite, latex particles, e.g., polystyrene, or carboxylated copolymers of styrene and butadiene, anionic phenolic resins and finely divided diazotized amino cellulose.

The known carriers are however limited in their applicability and usefulness in immunological diagnostic procedures since the corresponding immunological reagents show in many instances a lack of sensitivity and/or a poor stability.

In particular, it has not been possible to develop an agglutinationtest for the determination of myoglobin in the urine of patients with suspected myocardial infarction, because the known immunological carriers are not satisfying for attaching myoglobin under retention of its immunological properties or do not show a sufficient stability. The known methods for determining myoglobin in urine like the radial immunodiffusion are expensive and cumbersome. In particular, they do not allow a quick estimation of myoglobin in urine, which the physician could carry out at the bedside of the patient with suspected myocardial infaction.

There is thus a need for a carrier which will form, with a wide spectrum of immunologically active materials, in particular with myoglobin, a diagnostically useful reagent which is stable, specific, sensitive and provides an easily ascertainable visual or photometric evaluation in the minimum of time.

SUMMARY OF INVENTION

The present invention relates to a new latex polymer and a process for its manufacture. Furthermore, the invention relates to diagnostically useful reagents, a process for the manufacture thereof and diagnostic methods utilizing said reagents.

The present invention relates to a novel latex comprising discrete particles of a latex carrier to which a water-soluble polyhydroxy compound is covalently bound.

Furthermore, the present invention relates to a process for the manufacture of such a novel latex, comprising reacting an aqueous latex suspension with a water-soluble polyhydroxy compound.

Furthermore, the present invention relates to an activated latex manufactured by treating discrete particles of a latex carrier to which a water-soluble polyhydroxy compound is covalently bound with an activating agent.

Furthermore, the present invention relates to a water-insoluble immunological reagent having a specific gravity of about that of water, comprising discrete particles of a latex carrier to which a water-soluble polyhydroxy compound is covalently bound having condensed thereto, through a covalent link, a known immunologically active material.

Furthermore, the present invention relates to a process for the manufacture of such a water-insoluble immunological reagent, comprising reacting an immunologically active material with an activated latex manufactured by treating discrete particles of a latex carrier, to which a polyhydroxy compound is covalently bound, with an activating agent.

DETAILED DESCRIPTION

As used within the context of this invention, "latex carrier" or "core polymer" includes latex polymers which are water-insoluble, have a particle size in the range of from about 0.01 microns to about 0.9 microns, a specific gravity near that of water so that after coating with a polyhydroxy compound and coupling with the immunologically active material the specific gravity of the particles is about 1.0 (0.95-1.05), enabling them to remain permanently in aqueous suspension. The core polymer must be inert with respect to immunological diagnostic tests and must have active groups which are capable of forming a covalent linkage with a polyhydroxy compound. For example, the latex carriers can have carboxyl groups, amine groups or groups convertible into them. Typical suitable groups on the latex carriers are those containing an active hydrogen, e.g. —COOH, —CONH$_2$, a nitrile group, a primary amine group or a secondary amine group.

Any primary or secondary amine group can be utilized in accordance with the invention such as the amine groups can be —R—NH$_2$ or

wherein R is lower alkylene, i.e. alkylene radicals containing from 1 to 7 carbon atoms, R$_1$ is lower alkyl, i.e. alkyl radicals containing from 1 to 6 carbon atoms or R$_1$ and R$_2$ can be taken together with the attached nitrogen atoms to form an aromatic heterocyclic ring moiety of from 4 to 7 members containing the attached nitrogen as the only hetero atom such as pyridyl.

Typical suitable latex particles are those supplied commercially as an aqueous latex suspension, usually in concentrations of about 40% to about 60% solids. Many types of immunologically inert latex polymers are suitable for use in this invention provided they meet the criteria set forth above. This invention comprehends the use of all the suitable latex polymers.

Typical latex polymers which are suitable for this invention are those comprised of active hydrogen-containing polymers and copolymers of the following general compositions: polystyrene; polyvinyl pyridine; styrene-butadiene copolymers; acrylonitrile-butadiene copolymers; vinyl acetate-acrylate ester copolymers; vinyl chloride-acrylate ester copolymers. The various techniques of emulsion polymerization and further reaction of latex polymers offer a wide variety of means to incorporate into the latex particle the surface carboxyl, amine, amide, nitrile, etc. groups needed for coupling with the polyhydroxy compound. For example, surface carboxyl groups may be incorporated by adding to the monomer mixture a carboxyl-containing monomer, (e.g., acrylic acid, methacrylic acid, itaconic acid, aconitic acid, fumaric acid and maleic acid) or by a further chemical reaction of the latex polymer or copolymer surface in the latex state, (e.g., oxidation of surface hydroxyl end groups to carboxyl groups or hydrolysis of surface acrylate and methacrylate ester groups to carboxyl groups). Suitable latexes may be prepared by a wide variety of emulsion polymerization techniques: batch emulsion polymerization in which all of the ingredients are added to the polymerization reactor before the reaction is initiated; seeded emulsion polymerization in which a seed latex is added to the polymerization mixture to control the number of particles; semi-continuous emulsion polymerization in which the monomer mixture as well as other ingredients, (e.g., emulsifier and initiator solution) are added continuously or shotwise to the reaction mixture throughout the polymerization; continuous emulsion polymerization in which the ingredients are added to the reactor continuously and the latex is removed from the reactor continuously. One particularly suitable method for incorporating surface active hydrogen-containing groups is by seeded emulsion polymerization in which a monomer mixture containing an active hydrogen-containing monomer is polymerized on the surface of the seed latex particles.

Among the preferred latex polymers are carboxylated latex polymers like carboxylated styrene butadienes, carboxylated polystyrenes, carboxylated polystyrenes with amino groups, acrylic acid polymers, methacrylic acid polymers, acrylonitrile polymers, acrylonitrile butadiene styrenes, polyvinyl acetate acrylates, polyvinyl pyridines, vinyl chloride-acrylates and the like. Some commercially available latexes which are suitable for use in this invention are Amsco Res 4150, Amsco Res 3011 (American Mineral Spirits Co.); Dow Latex 815, Dow latex 816, Dow Latex 620, Dow Latex 859, Dow Latex CL 241 (The Dow Chemical Co.); Hycar 1512, Hycar 1571, Hycar 1877X8, Hycar 2600X120 (Goodrich Chemical Co.); Gelva 900, Lytron 612, Lytron 624 (Monsanto); Rhoplex LC40 3216, Amberlite Ultrafine (Rohm and Haas).

Particularly preferred latex polymers are carboxylated styrene butadienes.

The term "polyhydroxy compound" encompasses all compounds having at least two hydroxyl groups and capable to render the surface of the latex hydrophilic and suitable for covalent attachment of immunologically active materials. Possible polyhydroxy compounds are carbohydrates containing at least two free hydroxy groups and which may contain in addition to the hydroxy groups primary and/or secondary amine groups such as defined above and/or carboxyl groups. Preferred polyhydroxy compounds are water-soluble polysaccharides or derivatives thereof which contain hydroxyl groups, and/or primary and/or secondary amino groups and/or carboxyl groups. Examples of such polysaccharides are dextran, agarose, water-soluble cellulose derivatives, water-soluble starch or dextrin. Particularly preferred are polysaccharide derivatives like aminopolysaccharides, for example 1-amino-2-hydroxypropyldextran or p-aminophenoxyhydroxypropyldextran. Furthermore, copolymers of polysaccharides or other hydroxyl compounds with bifunctional substances, such as copolymers of saccharose with sugar alcohols like sorbitol or mannitol can also be used.

The term "immunologically active material" refers to components of physiological fluids, cell and tissue extracts for which an immunological counterreactant is available or can be produced. Typical immunological materials are primary amines, aminoacids, peptides, proteins, lipoproteins, glycoproteins, sterines, steroides, lipoides, nucleic acids, enzymes, hormones, vitamines, polysaccharides and alcaloides.

Examples of suitable immunologically active substances are given in the following table:

TABLE I

I. Microorganisms

Bacteria

1. Gram-positive cocci
   Streptococci (pyogenes, fecalis and viridans)
   Staphylococci (aureus and albus)
   Pneumococci (*D. pneumoniae*)
2. Gram-negative cocci
   Neisseria (gonorrhoeae and meningitidis)
3. Gram-positive aerobic bacilli
   Bacillus anthracis
   Corynebacterium diphtheriae
   Erysipelothrix
   Listeria monocytogenes
4. Gram-positive anaerobic bacilli
   Clostridia (botulinum, perfringens, welchii and tetani)
5. Gram-negative anaerobic bacilli
   Bacteroides
6. Gram-negative intestinal bacilli
   Escherichia
   Klebsiella
   Enterobacter
   Proteus
   Pseudomonas
   Salmonella
   Shigella
7. Gram-negative nonintestinal bacilli
   Pasteurella (pestis and tularensis)
   Hemophilus influenzae
   Brucella (melitensis, abortus and suis)
   Bordetella pertussis
   Malleomyces
8. Spirochetes
   *Treponema pallidum*
   Leptospira
   Borrelia
9. Mycoplasma
10. Mycobacteria
11. Vibrio
12. Actinomyces

Protozoa

1. Intestinal Protozoa
   Amebae
2. Flagellates
   Trichomonas
   Leishmania
   Trypanosomes
   Toxoplasma
3. Sporozoa
   Plasmodia (vivax, falciparum, malariae and ovale)
4. Intestinal nematodes
   Pinworms
   Hookworms
   Whip worms
5. Tissue nematodes
   Trichinella Filaria (*Wuchereria bancroftii*)
Dracunculus
6. Trematodes
   Schistosomes
   Intestinal flukes
   Tissue flukes
7. Cestodes
   Tapeworms
8. Toxoplasma (*T. gondii*)

Fungi

1. Sporotrichum
2. Cryptococcus
3. Blastomyces
4. Histoplasma
5. Coccidioides
6. Candida

Viruses and Rickettsia

1. Rickettsia
2. Viruses
   Canine hepatitis
   Shope papilloma
   Influenza A & B
   Fowl plaque
   Herpes simplex
   Adenoviruses
   Polyoma
   Rous sarcoma
Vaccinia
Poliovirus
Measles
Canine distemper
Leukemia
Mumps
Newcastle disease
Sendai
ECHO
Foot and mouth disease
Psittacosis
Rabies
Extromelia
Arbor viruses

II. Tissue antigens including organ specific antigens

Polysaccharides
Hyaluronidase
Tetanus toxin
Egg ovalbumin
Ovine serum albumin
Kidney
Liver
Skin
Heart (Myoglobin)
Gastrointestinal tract
Prostate
Embryonic antigens (alpha 1 fetoprotein)
Tumor antigens (carcinoembryonic antigen)
Muscle
Collagen
Amyloid

III. Hormones

Pituitary hormones
Insulin
Glucagon
Thyroid hormone
Chorionic gonatropin
Chorionic growth hormone—prolactin
Human placental lactogen

IV. Enzymes

Pancreatic chymotrypsinogen
Procarboxypeptidase
Deoxyribonuclease
Ribonuclease
Glyceraldehyde -3-phosphate dehydrogenase
Catalase
Peroxidase

V. Blood Cell Antigens, Blood Group Substances and other Isoantigens

Platelets
Megakaryocytes
Leucocytes
Erythrocytes
Blood group substances
Forssman antigen
Histocompability antigens

VI. Plasma Proteins

Fibrin and fibrinogen
Plasminogen and plasmin
Albumin
Immunoglobulins
$\alpha$-1-antichymotrypsin
$\alpha$-1-antitrypsin
Complement factors
Ceruloplasmin
Gc-globulin
Haptoglobin
$\alpha$-2-macroglobulin
$\beta$-2-microglobulin
Orosomucoid
Prealbumin
Transferrin

VII. Milk Proteins

Lactoferrin
Lysozyme
Secretory IgA
Secretory IgM
Secretory component

VIII. Saliva Proteins

Secretory IgA
Secretory IgM
Secretory component

IX. Urine Proteins

X. Pathologic Proteins

Myeloma protein
Macroglobulinaemic proteins
Dysglobulinaemic proteins
Bence Jones I, II proteins
C-reactive protein
Cryoglobulins

XI. Antibodies including autoantibodies

Antinuclear factor
Thyroid autoantibodies
Anti-Tamm-Horsfall protein
Cold agglutinins
Rheumatoid factor
Adrenal autoantibodies Autoantibody to gastric parietal cells in pernicious anemia
Anti-colon
Anti-liver
Anti-kidney
Autoantibodies to spermatozoa
Anti-heart
Muscle autoantibodies in myasthenia gravis
Autoantibodies to nervous tissue
Autoantibodies against fibrous tissue and vascular components
Autoantibodies against platelets and megakaryocytes
Antibodies against trophoblasts
Antibodies to microorganisms
Antibodies to animal antigens
Antibodies to drugs A particularly preferred immunologically active material is myoglobin, human placental lactogen, antibodies against IgG, or antibodies against myoglobin.

The novel latex of the present invention can be manufactured by reacting an aqueous latex suspension with a water-soluble polyhydroxy compound.

This can be achieved in a conventional manner depending on the active functional groups on the latex and the water-soluble polyhydroxy compound used.

In a preferred embodiment, in which the used latex is a carboxylated polymer and the water-soluble polyhydroxy compound an amino polysaccharide, the reaction, which involves the formation of an amide bond, is performed in the presence of a activating agent like a water-soluble carbodiimide, the Woodward reagent K(N-ethyl-5-phenyl-isoxazolium-3′-sulfonate) or a water-soluble chloroformiate.

Preferred coupling agents are water soluble carbodiimides of the formula $$R_2-N=C=N-R_3$$

wherein $R_2$ or $R_3$ are cycloalkyl, alkyl containing from 1 to 12 carbon atoms, aryl substituted lower alkyl, aryl, heterocyclic, heterocyclic-substituted lower alkyl and di-lower alkyl amino;
acid addition and quaternary amine salts thereof.

The term alkyl as used herein denotes straight and branched chain alkyl groups containing from 1 to 20 carbon atoms. The term lower alkyl designates straight and branched chain lower alkyl groups containing from 1 to 6 carbon atoms. The term cyclolower alkyl designates saturated cyclic saturated hyrocarbon groups containing from 3 to 7 carbon atoms such as cyclohexane, cycloheptane, cyclobutane, etc. The term aryl signifies mononuclear aromatic hydrocarbons such as phenyl and polynuclear aromatic hydrocarbon groups such as naphthyl. The term aryl also signifies heteroaromatic groups which contain a 4 to 7 membered ring and which contain in addition to carbon and hydrogen atoms from 1 or 2 hetero atoms selected from the group consisting of nitrogen, oxygen and mixtures thereof. Among the hetero aromatic moieties which can be utilized in accordance with this invention are included azepinyl, pyridyl, furyl, pyrrolyl, oxazolyl and imidazolyl. The term heterocyclic includes heterocyclic non-aromatic, 5 to 7 membered saturated ring which contains in addition to carbon and hydrogen from 1 to 2 hetero atoms selected from the group consisting of oxygen, nitrogen and mixtures thereof. Among the preferred heterocyclic ring structures are included morpholinyl, piperidinyl, tetrahydrofuryl, tetrahydropyranyl and pyrrolidinyl. Both the term aryl and heterocyclic includes ring structures which may be unsubstituted as well as substituted in 1, 2 or 3 positions with a lower alkyl substituent.

Particularly preferred coupling agents are water-soluble carbodiimides of the formula:

$$R_5-N=C=N-R_6$$

wherein $R_5$ or $R_6$ are: cycloalkyl having from 5 to 6 carbon atoms in the ring; alkyl of from 1 to 12 carbon atoms, e.g., methyl ethyl, n-propyl, isopropyl, n-butyl, sec.-butyl, isobutyl, tert.-butyl, amyl, hexyl, heptyl, octyl, nonyl, undecyl and dodecyl; monoarylsubstituted lower alkyl radicals, e.g., benzyl-$\alpha$- and $\beta$-phenylethyl; monoaryl radicals, e.g., phenyl; morpholino; piperidyl; morpholinyl substituted with lower alkyl radicals, e.g., ethyl morpholinyl; piperidyl substituted with lower alkyl radicals, e.g., ethyl piperidyl; di-lower alkylamino; pyridyl substituted with lower alkyl radicals, e.g., $\alpha$, $\beta$ and $\gamma$ methyl or ethyl pyridyl; acid addition salts; and quaternary amines thereof.

According to a preferred embodiment of this invention, the aminopolysaccharide and an aqueous suspension of the carboxylated core latex are reacted preferably at room temperature (about 20° C. to about 25° C.). Temperatures from about 0° C. to about 40° C., however, are suitable for the reaction. In order to insure a chemical coupling of the aminopolysaccharide to the core latex, a sufficient amount of the coupling agent is used to insure that a sufficient amount of amide bonds is formed. Generally, about 0.005 percent to about 6.0 percent by weight of a water-soluble carbodiimide, based on the weight of the particles, is suitable, usually, however, about 0.05 to 2.0 percent by weight is used.

The pH of the reaction can vary from 2 to 7 and is preferably from 4 to 5.

The order of adding the aminopolysaccharide, the carboxylated core latex and the coupling agent is not critical. However it is preferred to react in a first step the core latex polymer with the water-soluble coupling agent and to add in a second step the aminopolysaccharide.

The ratio of core latex to polyhydroxy compound in the resulting product can vary within broad limits and is preferably from 2 to 50 parts by weight, a ratio of 10 to 30 parts by weight being particularly preferred.

The novel reagent of the present invention can be manufactured by reacting the novel latex with an immunologically active material.

This can be achived in a conventional manner depending on the water-soluble polyhydroxy compound and the immunologically active material used. In a preferred embodiment the novel latex comprising discrete particles of a latex carrier to which a polyhydroxy compound is covalently bound is first activated, preferably with an oxidizing agent, and then reacted with the immunologically active material. Although the activated latex can be stored it is preferred to react it with the immunologically active material immediately after activation.

In a particularly preferred embodiment, in which the water-soluble polyhydroxy compound is an aminopolysaccharide, to avoid crosslinking problems later on, all the aminogroups of the aminopolysaccharide latex which are not involved in binding to the core are in a first step replaced by hydroxyl groups. This can be easily achieved through treatment with nitrous acid. The polysaccharide latex then is activated with periodate which oxidizes some of the glucose rings to dialdehydes. Excess periodate is reacted with ethylene glycol. After both reagents have been removed by washing, the such activated latex is reacted with the immunologically active material. To stabilize the Schiff's bases produced by the reaction of the amino groups of the immunologically active material with the activated latex and to eliminate unreacted aldehyde groups the product is mildly treated with sodium borohydride. This reduces Schiff's bases to amines and aldehyde groups to the corresponding alcohols without affecting significantly the biological activity of the immunologically active material. The excess of immunologically active material is preferably not unnecessarily exposed to reagents and is removed from the reaction mixture prior to the treatment with sodium borohydride. The activated latex is washed in the cold, but after addition of the immunologically active material the reaction is preferably allowed to proceed at roomtemperature. The reduction on the other hand is most conveniently carried out in an icebath at 0° C. to keep denaturation of the immunologically active material at a minimum. The final product is washed several times in buffer.

The amount of immunologically active material linked to the novel latex is usually from about 0.01% to 15.0% by weight. However, each particular immunologically active material is utilized in an amount in which it is most successfully employed in a diagnostic test. Therefore each material is combined with the carrier in a ratio suitable for its specific requirements. This invention therefore comprehends within its scope the use of an amount of immunologically active material in combination with an immunologically inert latex sufficient to provide a diagnostically effective reagent.

Once the product is formed, it can be utilized in specific diagnostic tests utitlizing immunological principles. It can be used in any convenient concentration depending on the specific test, however, concentrations of from about 0.5% to about 2.5% by weight are suitable with 1.2% by weight preferred. Thus, for example, the product formed when human myoglobin is coupled to the novel latex, can be used as a diagnostic reagent to determine myoglobinuria in a patient with suspected myocardial infarction. This can be accomplished, for example, by placing a drop of test urine on a clean glass slide, mixing it with a drop of appropriately dilute anti-human myoglobin serum, then adding a drop of the myoglobin-latex in aqueous suspension. Within a few minutes the results of the test are observed and are about 90-98% accurate.

The advantages of such a test are its simplicity, speed, specificity, accuracy and lack of false positives.

As another example, the product formed when sheep anti human IgG is coupled to the novel latex can be used as a diagnostic reagent to determine gamma globulin in serum or other body fluids.

The immunological reagent of the present invention can be used for the determination of immunoglogically active materials in a direct or in an indirect (inhibition) agglutinationtest or in the kinetic photometric method disclosed in the published German Patent Application No. 2749956 Corresponding to the U.S. Patent Application Ser. No. 849,926.

In the direct test the sample and the latex particles coated with the counterreagent for the immunologically active material to be determined are mixed and the agglutination observed visually or photometrically. The test is positive in case an agglutination takes place.

In the indirect test the sample is mixed with the counter-reagent (e.g. antiserum) for the material to be determined and then with latex particles coated with the same material. The agglutination is observed visually or photometrically. The test is positive in case no agglutination occurs.

The immunological reagents of the present invention can conveniently be packaged for commercial purposes e.g. in a diagnostic reagent kit.

In case of a direct test the reagent kit for the determination of a known immunologically active material contains in a container a water-insoluble immunological reagent having a specific gravity of about that of water comprising discrete particles of a latex carrier to which a water-soluble polyhydroxy compound is covalently bound having condensed thereto through a covalent link an immunological counterreagent for the immunologically active material to be determined.

In case of an indirect test the reagent kit for the determination of a known immunologically active material contains in a first container a water-insoluble immunological reagent having a specific gravity of about that of water comprising discrete particles of a latex carrier to which a water-soluble polyhydroxy compound is covalently bound having condensed thereto through a covalent link the immunologically active material to be determined; and in a second container an immunological counterreagent for the immunologically active material to be determined.

The following examples illustrate the invention.

EXAMPLE 1

Preparation of 1-Amino-2-hydroxypropyl-dextran

This soluble dextran derivative was prepared starting from the commercially available dextran fraction T 70 with an average molecular weight of 70,000 (Pharmacia). 2 g dextran T 70 was dissolved in 25 ml of water and 8.0 ml 1.0 N sodium-hydroxyde added. To this rapidly stirring solution 7.05 g epibromohydrin dissolved in 12.5 ml of dioxane was added at 30° C. and the mixture kept at this temperature for four hours. The suspension was then centrifuged for better phase separation and the lower phase pipetted off and discarded. The upper phase was cooled in an icebath and 40 ml 25% ammonia solution was added, as well as 10 ml 1.0 N hydrochloric acid. This reaction mixture was kept stirring at room temperature in a gastight flask for 20 hours. It was then dialyzed at 4° C. against 12 liters of distilled water containing 60 ml glacial acetic acid, followed by seven changes of distilled water. The dialyzed 1-amino-2-hydroxypropyldextran solution was concentrated to a volume of 34 ml by ultrafiltration. It was stabilized by the addition of 70 μl 20% sodium azide solution and stored in the refrigerator for further use.

Preparation of 1-Amino-2-hydroxypropyl-dextran T 70 coated latex

Carboxylated styrene butadiene Latex (Dow CL 241) was washed and freed from ammonia through treatment with the ionexchange resin Dowex AG 50-X8; Bio Rad (styrene divinyl benzene polymer latice carrying nuclear sulfonic acid groups) in the sodium form.

6 ml of this latex CL 241 in the Na+-form (solid content 78 mg/ml) was adjusted to pH 4.75. To the rapidly stirred suspension a solution of 10 mg CMC (1-cyclohexyl-3-[2-morpholinyl(4)-ethyl]carbodiimide-metho-p-toluenesulfonate) in 2 ml of water, prepared immediately before use, was added and after 3 minutes 2 ml of the 1-amino-2-hydroxypropyl dextran (T 70) solution at once. The pH was raised to 9.0 adding 0.1 N sodium hydroxide. After the suspension had been stirred at room temperature overnight its pH was 8.4. It was diluted with water to about 40 ml and centrifuged for 40 minutes at 45,000 times gravity. The latex was washed 3× with about 40 ml of water, then twice with 0.1 M sodium-borate buffer pH 8.5 and again twice with water. Finally the pellet was suspended in 20 ml of distilled water and 40 μl 20% sodiumazide solution was added for stabilization. From total hydrolysis of a latex sample and ninhydrin-reaction of the hydrolysis products comparing with the starting material it was calculated that 81% of the modified dextran was bound to the latex.

1,2-Dihydroxypropyl-dextran(T 70)coated latex

This derivative was prepared treating 1-amino-2-hydroxypropyl-dextran(T 70) coated latex with nitrous acid: To 5 ml of the final suspension of 1-amino-2-hydroxypropyl-dextran(T 70) coated latex 300 μl 1.0 N hydrochloric acid was added under stirring, followed by 100 μl of 1.5 M sodium nitrite in water. After the mixture had been reacted for five minutes at room temperature 250 μl 1.0 N sodiumhydroxyde was added. The suspension was diluted with water to about 12 ml and centrifuged for 40 minutes at 45,000×g. The latex was washed twice with about 12 ml of water and then taken up in 5 ml of water. For stabilization 10 μl 20% sodium azide was added.

Preparation of myoglobin-dihydroxypropyldextran(T 70)coated latex 35 ml dihydroxypropyldextran(T 70) coated latex was suspended in 7 ml 0.3 M sodium bicarbonate and 7 ml 0.1 M sodium periodate in distilled water was added. Shielded from the light the reaction mixture was stirred at room temperature for 30 min. Then 7 ml 0.25 M ethylene glycol was added and stirring continued for one hour. The mixture was then diluted to 40 ml with water and centrifuged for 30 min. at 45,000×g (at 2° C.). The supernatant was decanted and the latex washed once with about 40 ml icecold 0.01 M sodium carbonate buffer pH.9.5 centrifuging again for 30 minutes. The pellet now was taken up in 7 ml of icecold carbonate buffer.

To this activated latex a solution of 75 mg lyophilized myoglobin, dissolved in 3.5 ml carbonate buffer was added (corresponds to 70 mg myoglobin as determined spectrophotometrically). After adjusting its pH to 9.5 with 0.1 N sodiumhydroxide, the suspension was kept stirring at room temperature overnight (20 μl 20% sodium azide had been added for stabilization). It was then centrifuged 40 min. at 45,000×g. The supernatant with the excess myoglobin was pipetted off and saved for further experiments. The pellet was resuspended in 7 ml icecold sodium carbonate buffer and 14 ml of a freshly prepared 0.2% sodiumborohydride in carbonate buffer was added at 0° C. The reduction mixture was stirred in an icebath for 5 hours, then centrifuged (45 min. at 45,000×g) and the latex washed 4 times with about 40 ml 0.1 M glycine buffer pH 8.2. It was finally taken up in 35 ml glycine buffer, stabilized with 0.04% sodium azide. From the difference in optical density of the myoglobin solution before and after the coupling reaction it was calculated that about 25% of the protein was coupled.

Tube test

The tube test was carried out in veronal acetate buffer pH 8.2 (48 mM sodium acetate+48 mM sodium barbital.) 1.5 ml of diluted myoglobin antiserum (1:160) was mixed with 0.5 ml urine containing various amounts of myoglobin and 20 μl of the myoglobin latex. Urine containing 2.5 μg myoglobin/ml inhibited the agglutination for 90 minutes, whereas normal urine samples agglutinated in 40 minutes.

EXAMPLE 2

Coupling of sheep anti human IgG antibodies to 1,2-dihydroxypropyldextran(T 70)coated latex CL 241

5 ml deaminated latex as described in example 1 was centrifuged for 30 min. at 45,000×g. The supernatant was decanted and the latex suspended in 1 ml 0.3 M sodiumbicarbonate. 1 ml 0.1 M sodium periodiate in distilled water was added and shielded from the light the reaction mixture was stirred at room temperature during 30 minutes. Then 1 ml 0.25 M ethylene glycol in water was added and stirring continued for one hour. The mixture then was diluted to about 12 ml with water and centrifuged for 30 minutes (at 2° C.). The supernatant was decanted and the latex washed once with 12 ml icecold 0.01 M sodium carbonate buffer pH 9.5 centrifuging again for 30 min. The pellet now was suspended in 0.5 ml icecold 0.01 M sodium carbonate buffer and 1 ml of a sheep anti human IgG antibody solution in the same buffer containing 5.8 mg protein per ml was added. The reaction was allowed to proceed at 4° overnight. The suspension then was centrifuged and the supernatant with excess antibody pipetted off. The pellet was suspended in 1 ml icecold sodium carbonate buffer and 2 ml of a freshly prepared 0.2% sodium borohydride solution in carbonate buffer was added at 0° C. After stirring the reduction mixture for 4 hours in an icebath it was centrifuged and the supernatant was decanted. The latex then was washed three times with 12 ml of 0.1 M glycine buffer pH 8.2 stabilized with 0.04% sodium azide. It was finally taken up in 5 ml of the same buffer.

Tube test for human IgG

To 2 ml veronal buffered saline (3.13 mM barbital, 1.82 mM sodium barbital, 0.15 M sodium chloride pH 7.5) containing 0.75 μg human IgG 20 μl of the above latex suspension are added. Visible agglutination occurs within 75 min.

Slide test for human IgG

60 μl veronal buffered saline, containing 0.3 μg human IgG is mixed with 20 μl of the above latex suspension. Specific agglutination occurs within 30 seconds.

EXAMPLE 3

Coupling of human placental lactogen (HPL) to 1,2-dihydroxypropyldextran(T 70) coated latex CL 241

5 ml deaminated latex as described in example 1 was centrifuged for 30 min. at 45,000×g. The supernatant was decanted and the latex suspended in 1 ml 0.3 M sodium bicarbonate. 1 ml 0.1 M sodium periodate in distilled water was added and shielded from the light the reaction mixture was stirred at room temperature during 30 minutes. Then 1 ml 0.25 M ethylene glycol in water was added and stirring continued for one hour. The mixture then was diluted with water to about 12 ml and centrifuged for 30 min. (at 2° C.). The supernatant was decanted and the latex washed once with 12 ml icecold 0.01 M sodium carbonate buffer pH 9.5, centrifuging again for 30 minutes. The pellets now was suspended in 0.5 ml icecold carbonate buffer and 1 ml of a 1% human placental lactogen solution in water was added. The reaction was allowed to proceed at room temperature overnight. The mixture was then centrifuged for 40 minutes and the supernatant pipetted off. After suspending the pellet with 1 ml sodium carbonate buffer the reduction was performed at 0° C. with 2 ml of a freshly prepared 0.2% sodium borohydride solution in the same buffer. To this end the reduction mixture was stirred 4 hours in an icebath, then diluted with water to about 12 ml and centrifuged 40 minutes. The supernatant was decanted and the latex washed three times with 0.1 M glycine buffer pH 8.2. It was finally taken up in 5 ml of the same buffer, stabilized with 0.04% sodium azide.

Slide test for HPL

60 μl of phosphate buffered saline (PBS) are mixed with 20 μl of rabbit anti HPL serum diluted 1:20 with PBS and 20 μl of the above latex suspension. Agglutination is visible after 1 minute.

This agglutination can be specifically inhibited by mixing 20 μl antiserum (diluted 1:20 in PBS) first with 30 μl of PBS and 30 μl of the same buffer containing 3 μg HPL. No sign of agglutination is detected for more than 15 minutes.

Slide test

One drop or urine and one drop of antiserum were mixed with a plastic stirrer. Then one drop of latex was added, the sample mixed again with the stirrer and spread out evenly over the circle on the slide. The stopwatch was started while the mixture was kept in a circular motion. After two minutes the result was read. To obtain a sensitivity of 4 μg myoglobin per ml of urine the antiserum had to be diluted 1:13.3 using the same veronal buffer as in the tube test. The latex suspension had to be diluted 1:2.25 with glycine buffer.

I claim:

1. A latex composition comprising discrete particles of a latex carrier having reactive functional groups selected from a group consisting of carboxyl, amino, amido or nitrile, said latex particles being covalently bonded through said functional group to a polyhydroxy compound, said particles having a size in the range of from about 0.01 microns to about 0.9 microns and a specific gravity of about 1.0.

2. A latex composition comprising discrete particles of a latex carrier having a reactive functional group selected from the group consisting of carboxyl, amino, amido and nitrile, said latex particles being covalently bonded through said functional grop to a polyhydroxy compound, and said polyhydroxy compound being activated with an oxidizing agent, said particles having a size in the range of from about 0.01 microns to about 0.9 microns and a specific gravity of about 1.0.

3. The latex of claim 1 wherein said latex carrier is a carboxylated latex.

4. The latex of claim 3 wherein said carboxylated latex is a carboxylated styrene butadiene copolymer.

5. The latex of claim 1 wherein the water-soluble polyhydroxy compound is a water-soluble polysaccharide or a derivative thereof.

6. The latex of claim 5 wherein said water-soluble polysaccharide is an aminopolysaccharide.

7. The latex of claim 6 wherein the aminopolysaccharide is 1-amino-2-hydroxypropyldextran.

8. The latex of claim 1 wherein the ratio of said carrier latex to said water-soluble polyhydroxy compound is from about 2 to about 50 parts by volume.

9. The process for the production of a latex composition comprising reacting an aqueous suspension containing discrete particles of a latex carrier having reactive functional groups selected from the group consisting of amino, carboxyl, amido and nitrile with a water soluble polyhydroxy compound to covalently bond said polyhydroxy compound through said functional group to said latex particles, said particles having a size in the range of from about 0.01 to about 0.9 microns and a specific gravity of about 1.0.

10. A process for the manufacture of a latex composition comprising reacting an aqueous suspension containing discrete particles of a latex carrier having reactive functional groups selected from the group consisting of carboxyl, amino, amido and nitrile with a water soluble polyhydroxy compound to covalently bond said latex particles through said functional group to said polyhydroxy compound and thereafter treating said reacted latex particles with an oxidizing agent, said particles having a size in the range of from about 0.01 to about 0.9 microns and a specific gravity of about 1.0.

11. The latex of claim 10 wherein the oxidizing agent is a periodate.

12. The process of claim 9 wherein the latex is a carboxylated polymer and the water-soluble polyhydroxy compound an amino polysaccharide and said reaction is carried out in the presence of a coupling agent.

13. The process of claim 9 wherein the coupling agent is a water-soluble carbodiimide.

14. The process of claim 9 wherein activated latex reacted with the polyhydroxy compound is treated with an activating agent.

15. The process of claim 10 wherein said polyhydroxy compound is an amino polysaccharide and said reaction is carried out in the presence of a coupling agent.

* * * * *